United States Patent
Nakahara et al.

(10) Patent No.: US 12,372,729 B2
(45) Date of Patent: Jul. 29, 2025

(54) ENDOSCOPE OPTICAL CONNECTOR AND ENDOSCOPE

(71) Applicant: OLYMPUS MEDICAL SYSTEMS CORP., Tokyo (JP)

(72) Inventors: Kaito Nakahara, Hachioji (JP); Takuya Takechi, Aizuwakamatsu (JP); Tsutomu Urakawa, Hachioji (JP); Hiroki Takagi, Shiki (JP); Koichi Akahori, Hachioji (JP)

(73) Assignee: OLYMPUS MEDICAL SYSTEMS CORP., Tokyo (JP)

( * ) Notice: Subject to any disclaimer, the term of this patent is extended or adjusted under 35 U.S.C. 154(b) by 258 days.

(21) Appl. No.: 18/198,948

(22) Filed: May 18, 2023

(65) Prior Publication Data
US 2023/0288644 A1    Sep. 14, 2023

Related U.S. Application Data (63) Continuation of application No. PCT/JP2021/038809, filed on Oct. 20, 2021.

(51) Int. Cl.
*H04B 10/00* (2013.01)
*A61B 1/00* (2006.01)
*G02B 6/38* (2006.01)

(52) U.S. Cl.
CPC ........ *G02B 6/3849* (2013.01); *A61B 1/00126* (2013.01); *G02B 6/3897* (2013.01)

(58) Field of Classification Search
CPC .. G02B 6/3849; G02B 6/3897; G02B 6/3817; A61B 1/00126; A61B 1/00114;
(Continued)

(56) References Cited

U.S. PATENT DOCUMENTS

| 6,432,049 B1 * | 8/2002 | Banta ................... A61B 1/0669 600/245 |
| 11,892,124 B2 * | 2/2024 | McCormick .......... F17C 13/001 |

(Continued)

FOREIGN PATENT DOCUMENTS

| JP | S63-92318 U | 6/1988 |
| JP | 2000-126113 A | 5/2000 |

(Continued)

OTHER PUBLICATIONS

International Search Report dated Jan. 11, 2022 received in PCT/JP2021/038809.

*Primary Examiner* — Agustin Bello
(74) *Attorney, Agent, or Firm* — Scully, Scott, Murphy & Presser, P.C.

(57) ABSTRACT

An endoscope optical connector includes: a sleeve which houses an end portion of an optical fiber inside the sleeve; an inward flange provided on an inner circumference of the sleeve; a glass member arranged inside the sleeve so as to face an end surface of the optical fiber; a cap member which is attached to the sleeve and which fixes the glass member between the cap member and the inward flange; a first O-ring interposed between the cap member and the glass member; a second O-ring interposed between the glass member and the inward flange and having a glass transition point lower than a glass transition point of the first O-ring; and an inert gas filling the inside of the sleeve.

10 Claims, 9 Drawing Sheets

(58) Field of Classification Search
CPC .............. A61B 1/00117; A61B 1/0011; A61B 1/00124; A61B 1/07
See application file for complete search history.

(56) References Cited

U.S. PATENT DOCUMENTS

| | | | | |
|---|---|---|---|---|
| 12,083,353 | B2 * | 9/2024 | Altshuler | ................. A61N 5/06 |
| 2004/0184288 | A1 * | 9/2004 | Bettis | ................... A61B 1/0661 |
| | | | | 362/572 |
| 2008/0154254 | A1 * | 6/2008 | Burger | ................... A61B 18/02 |
| | | | | 606/23 |
| 2010/0073470 | A1 * | 3/2010 | Takasaki | ............... H04N 23/54 |
| | | | | 348/76 |
| 2015/0374207 | A1 | 12/2015 | Fukuoka | |
| 2016/0208149 | A1 * | 7/2016 | Kawasaki | .............. C09J 133/26 |
| 2020/0109226 | A1 * | 4/2020 | Hattori | .................... C08L 71/00 |
| 2020/0163717 | A1 * | 5/2020 | Hartkopf-Ceylan | ... A61B 18/24 |
| 2022/0331631 | A1 * | 10/2022 | Deurloo | ................. A62C 37/12 |
| 2023/0000320 | A1 * | 1/2023 | Kinouchi | ................. A61B 1/07 |
| 2023/0288644 | A1 * | 9/2023 | Nakahara | ................. A61B 1/07 |

FOREIGN PATENT DOCUMENTS

| | | |
|---|---|---|
| JP | 2001-149305 A | 6/2001 |
| JP | 2016-010497 A | 1/2016 |
| JP | 2018-047182 A | 3/2018 |
| JP | 6450873 B2 | 1/2019 |
| WO | 2017/094071 A1 | 6/2017 |
| WO | 2021/181620 A1 | 9/2021 |

* cited by examiner

| | FIRST O-RING | SECOND O-RING | 100°C | 25°C | −50°C |
|---|---|---|---|---|---|
| SAMPLE A | BUTYL RUBBER | BUTYL RUBBER | ○ | ○ | × |
| SAMPLE B | BUTYL RUBBER | ETHYLENE PROPYLENE RUBBER | ○ | ○ | ○ |

NO LEAKAGE IS DETECTED IN HELIUM LEAK TEST: ○
LEAKAGE IS DETECTED IN HELIUM LEAK TEST: ×

FIG. 8

| | FIRST O-RING | SECOND O-RING | 100°C | 25°C | −50°C |
|---|---|---|---|---|---|
| SAMPLE A | BUTYL RUBBER | BUTYL RUBBER | ◯ | ◯ | × |
| SAMPLE B | BUTYL RUBBER | ETHYLENE PROPYLENE RUBBER | ◯ | ◯ | ◯ |

NO LEAKAGE IS DETECTED IN HELIUM LEAK TEST: ◯
LEAKAGE IS DETECTED IN HELIUM LEAK TEST: ×

FIG. 9

| | FIRST O-RING | SECOND O-RING | 100 °C | 25 °C | −50 °C |
|---|---|---|---|---|---|
| SAMPLE A | BUTYL RUBBER | BUTYL RUBBER | ○ | ○ | × |
| SAMPLE B | BUTYL RUBBER | ETHYLENE PROPYLENE RUBBER | ○ | ○ | ○ |

NO LEAKAGE IS DETECTED IN HELIUM LEAK TEST: ○
LEAKAGE IS DETECTED IN HELIUM LEAK TEST: ×

ENDOSCOPE OPTICAL CONNECTOR AND ENDOSCOPE

CROSS-REFERENCE TO RELATED APPLICATION

This application is a continuation application of PCT/JP2021/038809 filed on Oct. 20, 2021, the entire contents of which are incorporated herein by this reference.

BACKGROUND OF THE INVENTION

1. Field of the Invention

The present invention relates to an endoscope optical connector configured to optically connect an endoscope to an external device, and also relates to an endoscope.

2. Description of the Related Art

Conventionally, electronic endoscopes have been widely spread in the fields of endoscopes. Such an electronic endoscope includes, at a distal end portion of an elongated insertion portion thereof, an image sensor such as a CMOS or the like. In recent years, in such a type of endoscope, high-pixelization of the image sensor has been underway.

However, achieving high-pixelization of an image sensor in an endoscope leads to an increase of amounts of signals such as video signals that are transmitted from the image sensor to a signal processing apparatus (processor). To address such a circumstance, a signal transmission method using an optical fiber is employed also in an endoscope system. Employing the signal transmission method using the optical fiber enables high-speed transmission of large-capacity signals while suppressing an increase of a diameter size of a signal line to maintain a reduced diameter of an insertion portion.

In such a transmission method, in general, a signal such as an image signal is converted into an optical signal, and thereafter transmitted to an endoscope connector through an optical fiber. Furthermore, the optical signal transmitted to the endoscope connector is transmitted to a processor by optically connecting an optical connector provided in the endoscope connector and an optical connector provided in the processor.

The optical connector on the endoscope side may cause attenuation of optical signals if a medicinal solution or water vapor intrude into the optical connector during cleaning processing, disinfection processing, and sterilizing processing of the endoscope.

In order to address such a problem, a technique disclosed, for example, in Japanese Patent Application Laid-Open Publication No. 2018-47182 is used to solder a sapphire glass to a distal end of an optical connector to thereby be capable of sealing the optical connector.

SUMMARY OF THE INVENTION

An endoscope optical connector according to one aspect of the present invention includes: a cylindrical member configured to house an end portion of an optical transmission member inside the cylindrical member; a positioning member provided on an inner circumference of the cylindrical member; a light-passing member arranged inside the cylindrical member so as to face an end surface of the optical transmission member; a fixing member attached to the cylindrical member, and configured to fix the light-passing member between the fixing member and the positioning member; a first elastic sealing member interposed between the fixing member and the light-passing member; a second elastic sealing member interposed between the light-passing member and the positioning member, the second elastic sealing member having a glass transition point lower than a glass transition point of the first elastic sealing member; and gas filling the inside of the cylindrical member.

An endoscope according to one aspect of the present invention includes an optical connector as an endoscope connector. The optical connector includes: a cylindrical member configured to house an end portion of an optical transmission member inside the cylindrical member; a positioning member provided on an inner circumference of the cylindrical member; a light-passing member arranged inside the cylindrical member so as to face an end surface of the optical transmission member; a fixing member attached to the cylindrical member, and configured to fix the light-passing member between the fixing member and the positioning member; a first elastic sealing member interposed between the fixing member and the light-passing member; a second elastic sealing member interposed between the light-passing member and the positioning member, the second elastic sealing member having a glass transition point lower than a glass transition point of the first elastic sealing member; and gas filling the inside of the cylindrical member.

An endoscope optical connector according to another aspect of the present invention includes: a cylindrical member configured to house an end portion of an optical transmission member inside the cylindrical member; a positioning member provided on an inner circumference of the cylindrical member; a light-passing member arranged inside the cylindrical member so as to face an end surface of the optical transmission member; a fixing member attached to the cylindrical member, and configured to fix the light-passing member between the fixing member and the positioning member; a first elastic sealing member interposed between the fixing member and the light-passing member; a second elastic sealing member interposed between the light-passing member and the positioning member; and gas filling the inside of the cylindrical member. The first elastic sealing member has a higher resistance to degradation due to chemicals than the second elastic sealing member, and the second elastic sealing member ensures a higher sealability between the cylindrical member and the light-passing member under an environment of a temperature of −50° C. than the first elastic sealing member.

DETAILED DESCRIPTION OF THE PREFERRED EMBODIMENT(S)

Hereinafter, an embodiment of the present invention will be described with reference to drawings, Note that a different scale size is used for each of the constituent elements in the drawings to be used for the description below in order to illustrate each of the constituent elements in a recognizable size on each of the drawings. The present invention is not limited only to the number, the shapes, the ratio of the sizes of the constituent elements, and the relative positional relationship among the respective constituent elements shown in the respective drawings.

Figure 1:
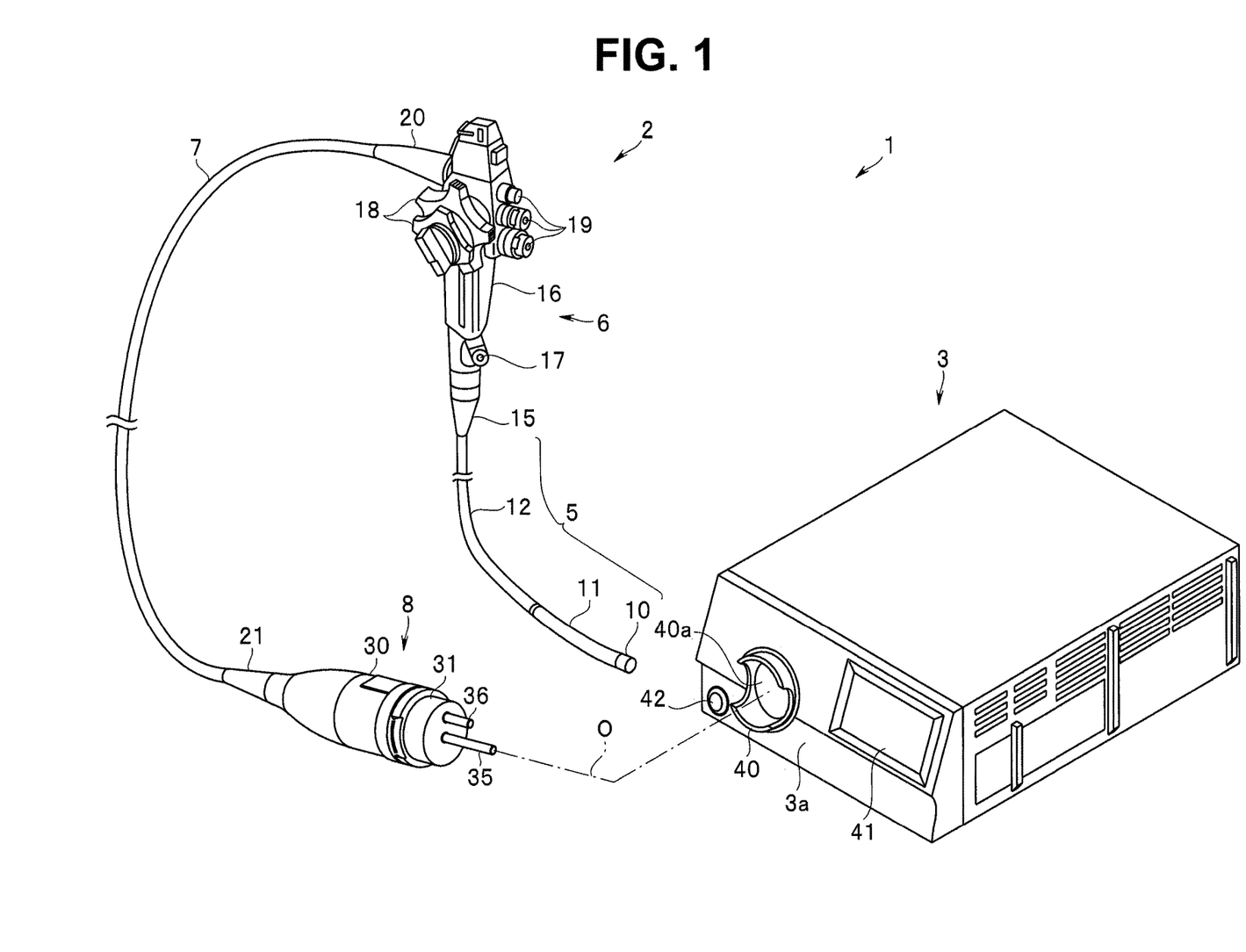
FIG. 1 is a perspective view showing an endoscope system.

FIGS. 1 to 9 relate to an embodiment of the present invention. As shown in FIG. 1, an endoscope system 1 in the present embodiment includes an endoscope 2 and an endoscope processor 3.

The endoscope 2 includes an insertion portion 5 configured to be insertable into a subject such as a human body, an operation portion 6 provided continuously with the proximal end side of the insertion portion 5, and a universal cable 7 which is a composite cable extended from a side surface of the operation portion 6, and an endoscope connector 8 provided at an end portion of the universal cable 7.

The insertion portion 5 includes a rigid distal end portion 10, a bending portion 11 provided continuously with the proximal end side of the distal end portion 10, and a flexible tube portion 12 provided continuously with the proximal end side of the bending portion 11. The distal end portion 10, the bending portion 11, and the flexible tube portion 12 are connected in this order from the distal end side.

In the present embodiment, the distal end portion 10 includes, on the distal end surface thereof, an observation window, an illumination window, and a treatment instrument channel port (none of them are shown).

Inside the distal end portion 10, an image pickup unit 50 (see FIG. 5) is provided on the rear surface side of the observation window. The image pickup unit 50 includes, for example, an image pickup device 51 constituted of a CCD or a CMOS, and a transmission module 52. In addition, the image pickup unit 50 is connected with one end of an optical fiber 36a as an optical transmission member. A signal such as an image signal, which is obtained by image pickup by the image pickup device 51, is converted into an optical signal by the transmission module 52 to be incident on the optical fiber 36a.

Furthermore, inside the distal end portion 10, one end of a light guide bundle 35a (see FIG. 2) is disposed on the rear surface side of the illumination window.

Furthermore, inside the distal end portion 10, one end of a treatment instrument channel, not shown, is connected to the treatment instrument channel port.

The respective other end sides of the optical fiber 36a, the light guide bundle 35a, and the treatment instrument channel are extended into the inside of the operation portion 6 via the insides of the bending portion 11 and the flexible tube portion 12.

The operation portion 6 includes, on the distal end side thereof, a break prevention member 15 configured to cover the outer circumferential portion on the proximal end side of the flexible tube portion 12. In addition, the operation portion 6 includes, at a midway part thereof, a grasping portion 16 configured to be grasped by a user or the like when using the endoscope. Between the break prevention member 15 and the grasping portion 16, a treatment instrument insertion port 17 that configures the proximal end side opening of the treatment instrument channel is provided. The operation portion 6 further includes, on the proximal end side with respect to the grasping portion 16, a bending operation knob 18 and various switches 19. The bending operation knob 18 is configured to bend the bending portion 11 in up, down, left, and right directions. Various functions of the endoscope 2 are assigned to the switches 19.

The universal cable 7 includes break prevention members 20, 21 provided respectively on both end portions connected respectively to the operation portion 6 and the endoscope connector 8. The break prevention members 20, 21 cover the outer circumferential portion of the universal cable 7 to maintain the connection strength, to thereby prevent a damage on the universal cable 7 due to twisting and the like. The above-described optical fiber 36a and the light guide bundle 35a are inserted through the inside of the universal cable 7. Furthermore, inside the universal cable 7, a wiring for power source, a wiring for signal, and the like (none of them are shown) are inserted. The wiring for power source is used for supplying power source from the endoscope processor 3 to the image pickup unit and the like. The wiring for signal is used for conveying a control signal from the endoscope processor 3 to the image pickup unit and the like.

Figure 2:
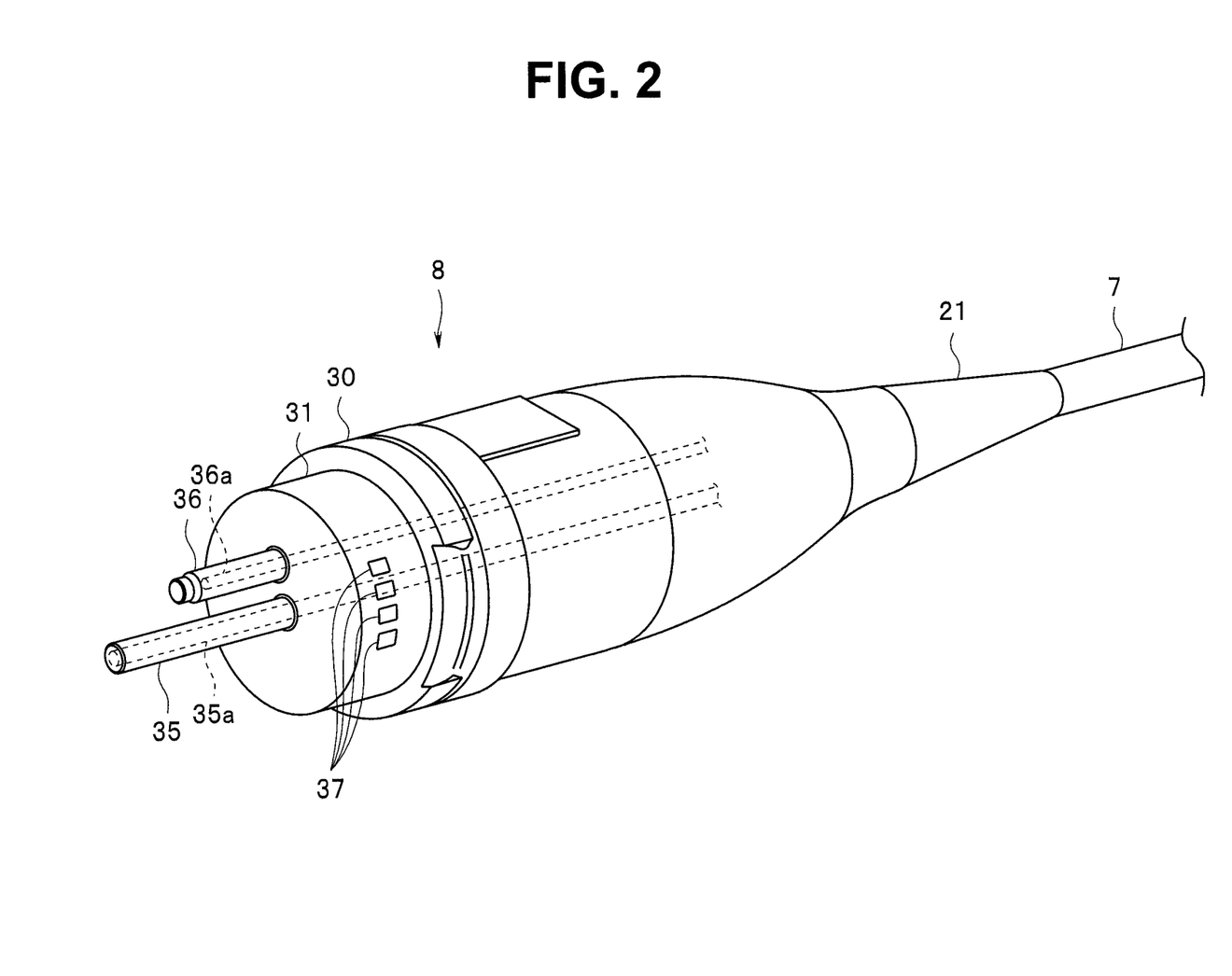
FIG. 2 is a perspective view showing an endoscope connector.

The endoscope connector 8 includes a connector main body 30 having a substantially cylindrical shape and a cylindrical portion 31 protruding from the distal end surface of the connector main body 30. Note that the basic shape of the endoscope connector 8 is not limited to the substantially cylindrical shape, but may be a cylindrical shape such as a substantially polygonal cylindrical shape. The endoscope connector 8 in the present embodiment is configured to be inserted into a receptacle 40 to be described later along a direction of a central axis O. Therefore, in the description below, the central axis O is appropriately referred to as an insertion axis O.

Figure 4:
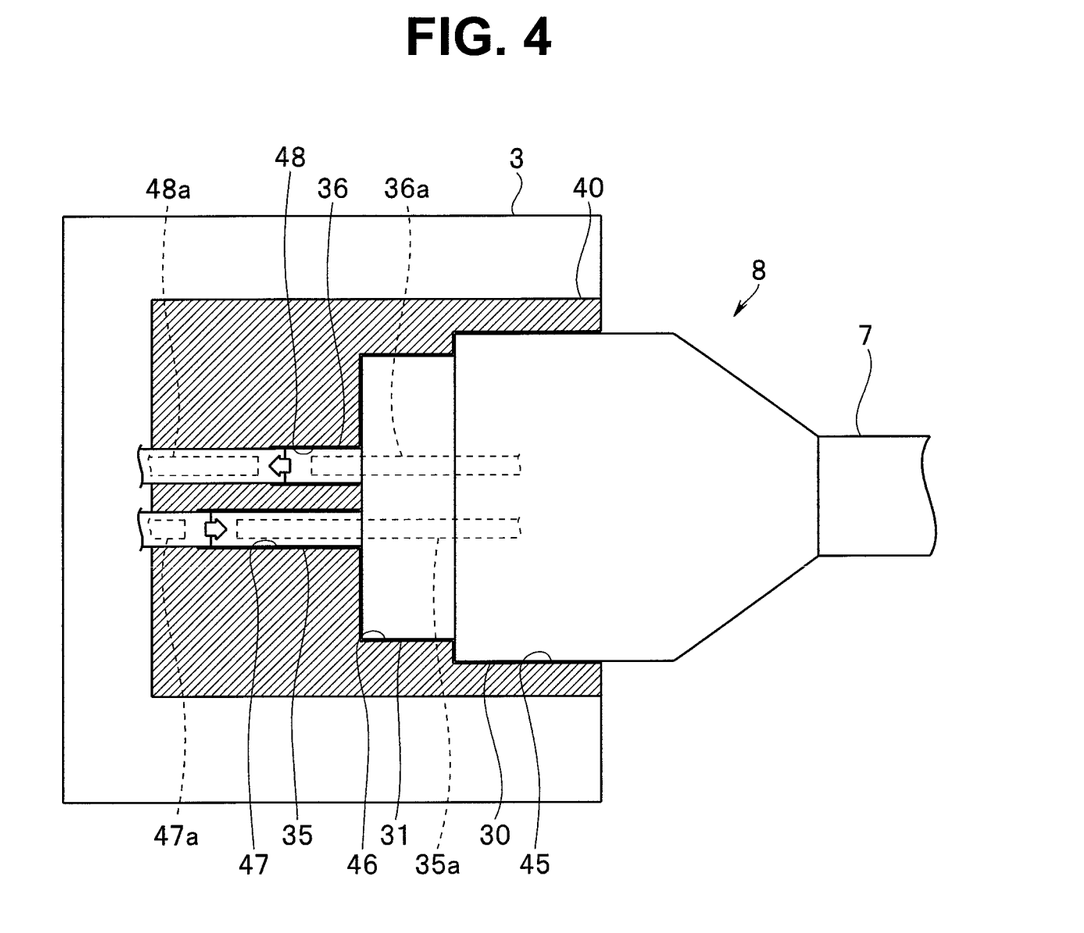
FIG. 4 is a schematic view of the endoscope connector connected to the receptacle.

As shown in FIGS. 2 and 4, a light guide plug 35 and an optical connector plug 36 are protruded from the distal end surface of the cylindrical portion 31 of the endoscope connector 8 in the direction of the central axis O of the endoscope connector 8. The light guide plug 35 holds, inside thereof, the other end portion of the light guide bundle 35a. The optical connector plug 36 holds, inside thereof, the other end portion of the optical fiber 36a.

The optical connector plug 36 functions as an optical connector configured to contactlessly convey an optical signal (a signal such as an image pickup signal), which is incident on the one end of the optical fiber 36a from the transmission module 52 of the image pickup unit 50, to the endoscope processor 3 without using an electric contact.

Furthermore, a plurality of electric contacts 37 are provided on the outer circumferential surface of the cylindrical portion 31. Some of these electric contacts 37 are used for power source and others are used for a control signal, for example. The electric contacts 37 for power source are connected to the wiring for power source inside the endoscope connector 8. The electric contacts 37 for control signal are connected to the wiring for signal inside the endoscope connector 8.

The endoscope processor 3 includes, on a front surface 3a thereof, the receptacle 40, a touch panel 41, and a power source switch 42. The receptacle 40 serves as a connector receiver to which the endoscope connector 8 is connectable. The touch panel 41 is configured to display operations and states. Note that the processor 3 incorporates inside thereof a light source for illumination, such as a halogen lamp, not shown.

Figure 3:
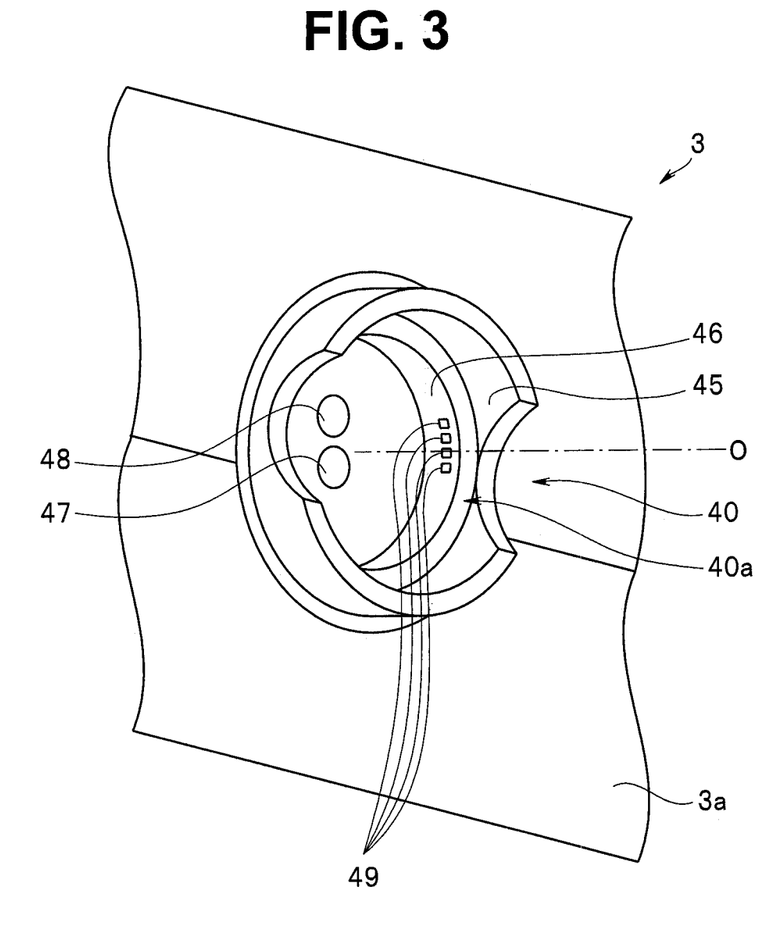
FIG. 3 is a perspective view showing a receptacle.

As shown in FIG. 3, the receptacle 40 includes a connector receiver hole 40a into which the endoscope connector 8 is insertable. The connector receiver hole 40a includes a receiver hole main body 45 having a substantially cylindrical shape, and a cylindrical hole 46 which is recessed on the proximal end surface (which is the proximal end surface when the opening portion side of the connector receiver hole 40a is defined as the distal end side) of the receiver hole main body 45.

The respective inner diameters of the receiver hole main body 45 and the cylindrical hole 46 are set to be slightly larger than the respective outer diameters of the connector main body 30 and the cylindrical portion 31 of the endoscope connector 8. The depth of the cylindrical hole 46 is set to be substantially coincident with the protruding length of the cylindrical portion 31 of the endoscope connector 8. Such a configuration enables the distal end side of the endoscope connector 8 to be fitted into the connector receiver hole 40a of the receptacle 40.

The basic shape of the connector receiver hole 40a is not limited to the substantially cylindrical shape. When the endoscope connector 8 has a cylindrical shape such as a substantially polygonal cylindrical shape, or the like, the connector receiver hole 40a may have a cylindrical shape corresponding to the shape of the endoscope connector 8.

The cylindrical hole 46 includes, on the proximal end surface thereof, a light guide insertion hole 47 into which the light guide plug 35 is insertable, and an optical fiber insertion hole 48 into which the optical fiber plug 36 is insertable. The light guide insertion hole 47 and the optical fiber insertion hole 48 are hole portions extending along the direction of the insertion axis O, for example.

The light guide insertion hole 47 is provided at a position corresponding to the light guide plug 35 protruding from the endoscope connector 8. In the deep part of the light guide insertion hole 47, a light guide bundle 47a for emitting illumination light to the light guide plug 35 is provided.

In addition, the optical fiber insertion hole 48 is provided at a position corresponding to the optical fiber plug 36 protruding from the endoscope connector 8. In the deep part of the optical fiber insertion hole 48, an optical fiber 48a for receiving an optical signal emitted from the optical fiber plug 36 is provided.

Furthermore, the cylindrical hole 46 includes, on the inner circumferential surface thereof, electric contacts 49 provided at positions corresponding to the respective electric contacts 37.

Next, description will be made on an optical signal transmission system in the endoscope system 1 configured as described above.

Figure 5:
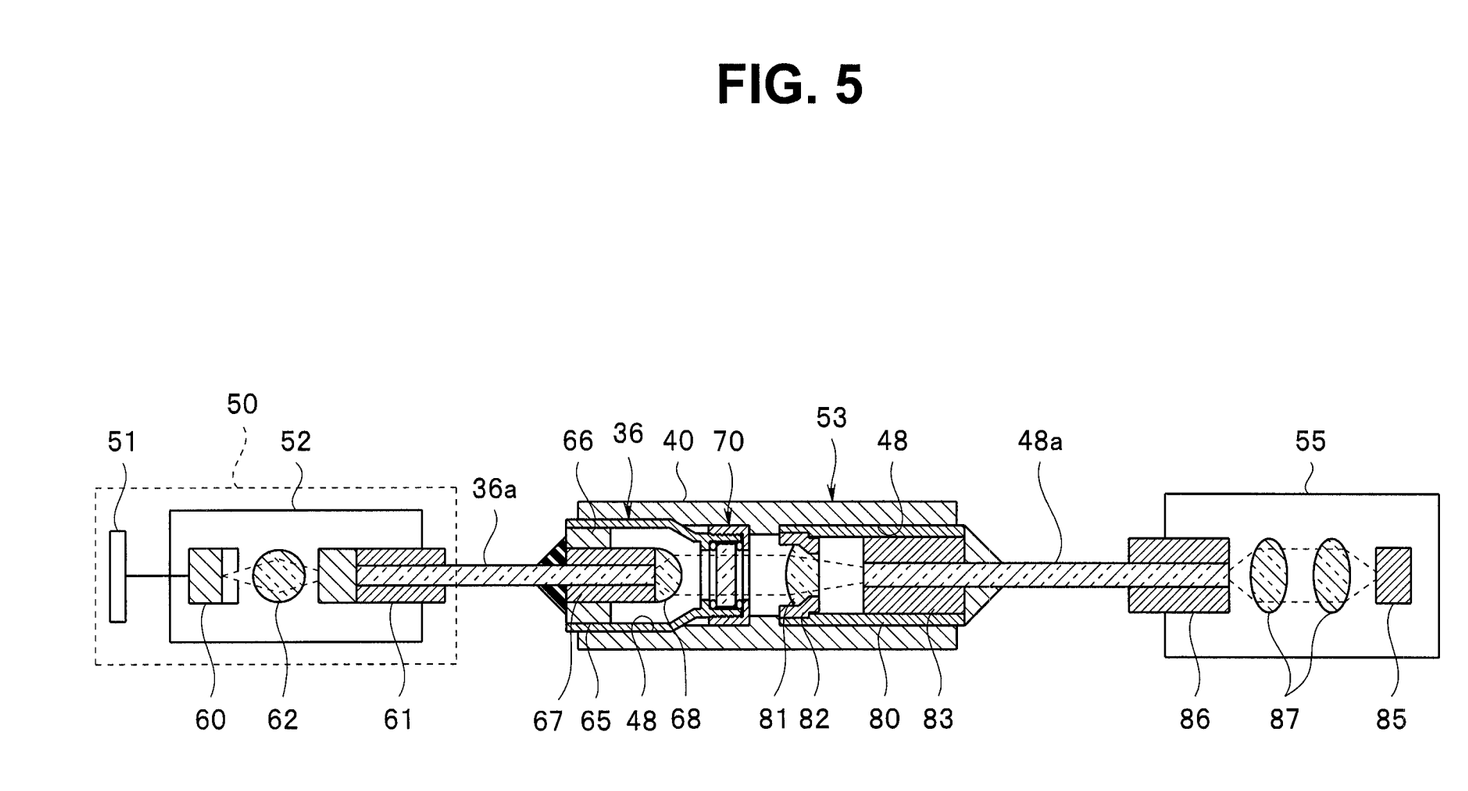
FIG. 5 is a schematic view showing an optical signal transmission system which is used in the endoscope system.

The optical signal transmission system according to the present embodiment includes the transmission module 52, the optical connector plug 36 connected to the transmission module 52 through the optical fiber 36a, an optical connector socket 53 configured to be optically connectable to the optical connector plug 36, and a reception module 55 connected to the optical connector socket 53 through the optical fiber 48a.

The transmission module 52 includes a light-emitting element 60 for converting a signal (electric signal) such as an image signal inputted from the image pickup device 51 into an optical signal.

In the transmission module 52, one end portion of the optical fiber 36a is held, through a ferrule 61, at a position opposed to the light-emitting element 60.

Furthermore, the transmission module 52 includes a condensing lens 62 configured to condense the optical signal emitted from the light-emitting element 60 to cause the optical signal to be incident on the end surface (one end surface) of the optical fiber 36a.

Figure 6:
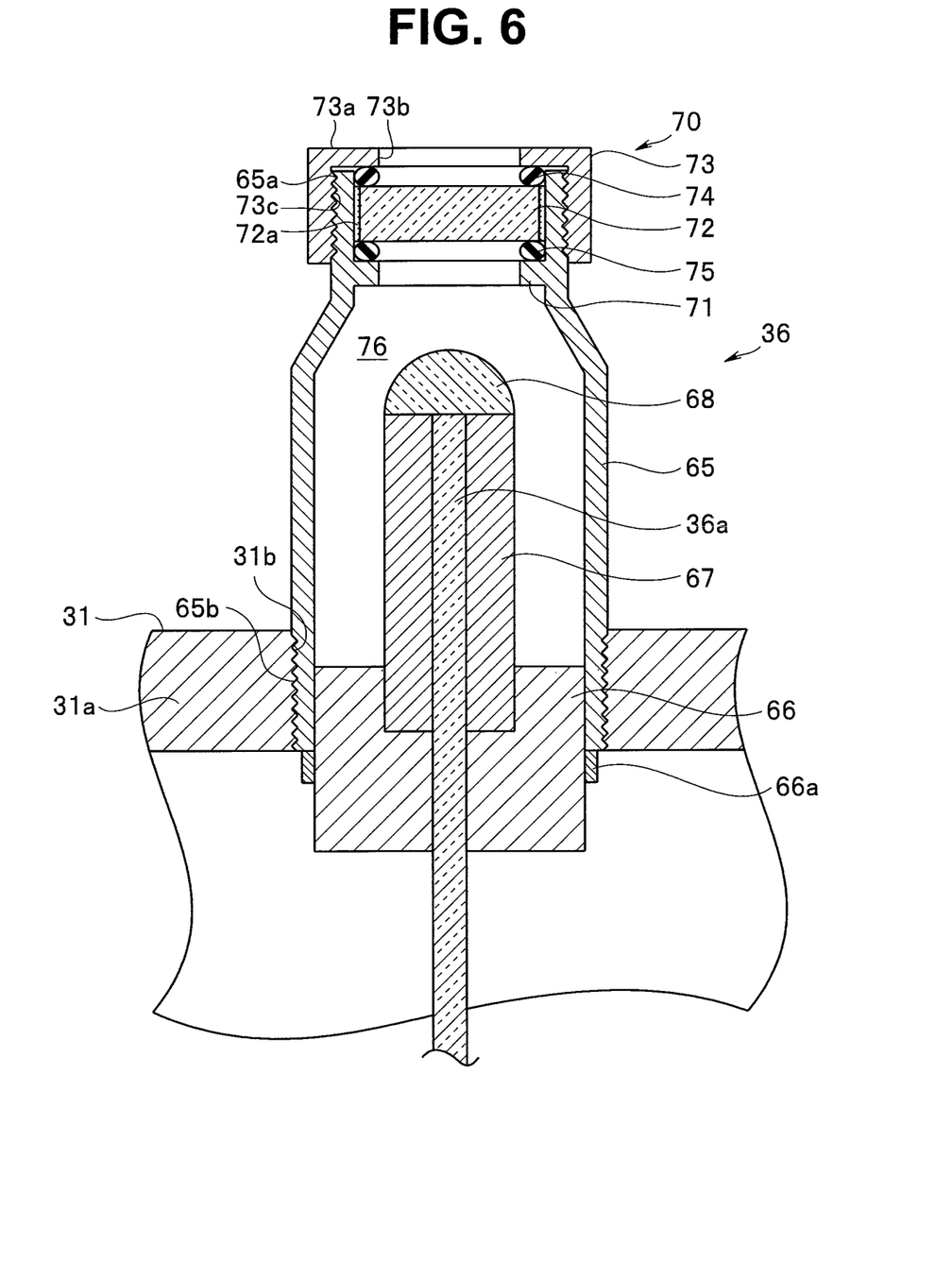
FIG. 6 is a schematic view showing an optical connector.

As shown in FIGS. 5 and 6, the optical connector plug 36 includes a sleeve 65 which is a metal cylindrical member. The sleeve 65 is provided in the cylindrical portion 31 of the endoscope connector 8. More specifically, the proximal end side of the sleeve 65 is fixed, by a male screw portion 65b provided on the outer circumference on the proximal end side of the sleeve 65 being screwed into a female screw portion 31h provided on an exterior-most portion 31a of the cylindrical portion 31.

In addition, a rear end member 66 is provided on the inner circumference on the proximal end side of the sleeve 65. The rear end member 66 is air-tightly connected to the sleeve 65 by a welded portion 66a formed, by seam welding, between the rear end member 66 and the sleeve 65.

The optical fiber 36a is penetrated through the rear end member 66. The optical fiber 36a is thus penetrated, and thereby the other end side of the optical fiber 36a is protruded to the inside of the sleeve 65.

The optical fiber 36a is supported by the rear end member 66 through the ferrule 67 inside the sleeve 65.

In addition, a condensing lens 68 is provided on the end surface (the other end surface) of the optical fiber 36a. The condensing lens 68 is configured to increase a light flux diameter of the optical signal emitted from the optical fiber 36a, to collimate the light.

Note that a seal member (not shown), for example, which is made of a resin block having elasticity, is crimped to the proximal end surface of the rear end member 66. The optical fiber 36a is penetrated through the seal member, with the optical fiber 36a air-tightly contacting the seal member. Such a configuration achieves the air-tight sealing of the proximal end side of the optical connector plug 36.

In addition, on the distal end side of the sleeve 65, a sealing unit 70 for air-tightly sealing the sleeve 65 is provided.

The sealing unit 70 includes an inward flange 71 as a positioning member, a glass member 72 as a light-passing member, a cap member 73 as a fixing member, a first O-ring 74 (hereinafter, O-ring includes an O-shaped rubber washer) as a first elastic sealing member, and a second O-ring 75 as a second elastic sealing member.

The inward flange 71 is formed on the distal end side of the sleeve 65 so as to be integral with the inner circumference of the sleeve 65.

The glass member 72 has a thickness of 3 mm, for example. As the glass member 72, for example, a tempax glass (TEMPAX Float® (registered trademark)), which is a borosilicate glass, is preferably employed. Note that such a glass member is less expensive than a sapphire glass subjected to a metallization treatment.

The cap member 73 includes a substantially disk-shaped cap main body 73a and a female screw portion 73c, for example. The cap main body 73a has an opening portion 73b whose diameter is substantially equal to the inner diameter of the inward flange 71. The female screw portion 73c is formed integrally with the edge portion of the cap main body 73a.

The cap member 73 is fixed to the sleeve 65 by the female screw portion 73c being screwed to the male screw portion 65a provided on the outer circumference on the distal end side of the sleeve 65 with a predetermined torque.

The first O-ring 74 is disposed between the glass member 72 and the cap member 73.

Furthermore, the second O-ring 75 is disposed between the glass member 72 and the inward flange 71.

The first O-ring 74 and the second O-ring 75 are compressed between the cap member 73 and the inward flange 71, to be elastically deformed, when the cap member 73 is attached to the sleeve 65. Specifically, the first O-ring 74 and the second O-ring 75 are elastically deformed until the O-rings are flattened by approximately 30% to 40% relative to their natural state.

Such an elastic deformation brings the first O-ring 74 and the second O-ring 75 into close contact with the inner circumferential surface of the sleeve 65 and the edge portion of the glass member 72, to thereby achieve a liquid-tight sealing between the sleeve 65 and the glass member 72.

In the present embodiment, the first O-ring 74 is configured by including, for example, a material having a higher resistance to degradation due to chemicals than that of the second O-ring 75. More specifically, in the present embodiment, the first O-ring 74 is configured by including a butyl rubber.

The butyl rubber, for example, has a water vapor permeability of 16 $g/m^2$·day and a water vapor permeability coefficient of 16 $g·mm/m^2$·day, when a sample thickness is 1.041 mm under the environment of the temperature of 85° C. and the humidity of 85% Rh. In addition, the butyl rubber has a heat resistance limit temperature of 150° C. and a glass transition point of −50° C. The heat resistance limit temperature indicates an upper limit of a limit temperature at which the physical properties of the butyl rubber can be maintained.

In addition, the second O-ring 75 is configured by including, for example, a material having a glass transition point lower than that of the first O-ring 74. More specifically, in the present embodiment, the second O-ring 75 is configured by including an ethylene propylene rubber.

The ethylene propylene rubber, for example, has a water vapor permeability of 93 $g/m^2$·day and a water vapor permeability coefficient of 96 $g·mm/m^2$·day, when a sample thickness is 1.036 mm under the environment of the temperature of 85° C. and the humidity of 85% Rh. In addition, the ethylene propylene rubber has a glass transition point of −60° C.

The sealing unit 70 thus configured is assembled to the sleeve 65 in an atmosphere of the gas with low humidity, for example.

Specifically, in an atmosphere of an inert gas such as an argon gas (or nitrogen with low humidity, the second O-ring 75, the glass member 72, and the first O-ring 74 are sequentially inserted into the sleeve 65 which is heated up to a predetermined temperature.

This enables a gaseous body inside the sleeve 65 to be replaced from an air with high humidity to the argon gas with low humidity, or the like.

At that time, an adhesive 72a is applied between the outer circumferential surface of the glass member 72 and the inner circumferential surface of the sleeve 65. An adhesive made of an epoxy resin, or the like, is preferably used as the adhesive 72a.

Then, the female screw portion 73c of the cap member 73 is screwed to the male screw portion 65a of the sleeve 65 with the predetermined torque using a torque driver, or the like, to thereby cause the cap member 73 to be attached to the distal end side of the sleeve 65.

As a result, the sleeve 65 is sealed, with the inside of the sleeve 65 being filled with an inert gas 76. In other words, the first O-ring 74 and the second O-ring 75 are elastically deformed between the inward flange 71 and the cap member 73, to thereby bring the first O-ring 74 and the second O-ring 75 into close contact with the inner circumferential surface of the sleeve 65 and the edge portion of the glass member 72, and the distal end side of the sleeve 65, inside of which is filled with a gas, i.e., the inert gas 76, is sealed. In this case, it is preferable that the inert gas 76 accounts for 80% or more of the volume of the gaseous body in the sleeve 65.

The optical connector socket 53 includes a sleeve 80, a condensing lens 81, and a ferrule 83. The sleeve 80 is held in the optical fiber insertion hole 48. The condensing lens 81 is held inside the sleeve 80, through a lens frame 82, at a position on the one end side of the sleeve 80. The ferrule 83 is configured to hold the one end side of the optical fiber 48a inside the sleeve 80, at a position on the other end side of the sleeve 80.

The condensing lens 81 is positioned at a location where the condensing lens 81 can condense the optical signal emitted from the optical connector plug 36, to cause the optical signal to be incident on the end surface (one end surface) of the optical fiber 48a. With such a configuration, when the optical connector plug 36 is inserted into the optical fiber insertion hole 48, the optical connector plug 36 and the optical connector socket 53 are optically connected to each other.

The reception module 55 includes a light-receiving element 85, a ferrule 86, and a condensing lens 87. The light-receiving element 85 is configured to convert the optical signal transmitted by the optical fiber 48a into an electric signal. The ferrule 86 is configured to hold the other end side of the optical fiber 48a at a position opposed to the light-receiving element 85. The condensing lens 87 is configured to condense the optical signal emitted from the end surface (the other end surface) of the optical fiber 48a to cause the optical signal to be incident on the light-receiving element 85.

According to such an embodiment, the optical connector plug 36 of the endoscope 2 includes: the sleeve 65 configured to house, inside thereof, the end portion of the optical fiber 36a; the inward flange 71 provided on the inner circumference of the sleeve 65; the glass member 72 arranged inside the sleeve 65 so as to face the end surface of the optical fiber 36a; the cap member 73 attached to the sleeve 65 and configured to fix the glass member 72 between the cap member 73 and the inward flange 71; the first O-ring 74 interposed between the cap member 73 and the glass member 72; the second O-ring 75 interposed between the glass member 72 and the inward flange 71 and having the glass transition point lower than that of the first O-ring 74; and the inert gas 76 filling the inside of the sleeve 65.

Such a configuration can prevent the intrusion of a medicinal solution and water vapor into the optical connector plug 36 and also can prevent the moisture condensation in the inside of the optical connector plug 36 at a low cost. Therefore, such a configuration can prevent adherence of liquid droplets to the glass member, to thereby enable the optical signal transmitted from the optical fiber 36a to be conveyed to the processor 3 without attenuation.

In other words, at least two kinds of O-rings 74 and 75 having different glass transition points are used to achieve the sealing between the sleeve 65 and the glass member 72, to thereby surely ensure the sealability between the sleeve 65 and the glass member 72 not only in the case where rapid temperature changes occur due to the cleaning processing, the disinfecting processing, the sterilizing processing, and the like but also in the case where the optical connector plug 36 is cooled to an extremely low temperature by the air transportation of the endoscope 2, for example.

In addition, the inside of the optical connector plug 36 (sleeve 65) is filled with the gas, to thereby surely prevent the occurrence of the moisture condensation in the inside of the optical connector plug 36 even in the case where rapid temperature changes occur due to the cleaning processing, the disinfecting processing, the sterilizing processing, and the like.

More specifically, the first O-ring 74, which seals the part of the optical connector plug 36 on the distal end side with respect to the glass member 72, is made of the butyl rubber having the heat resistance limit temperature of 150° C., the glass transition point of −50° C., and the high resistance to degradation due to the chemicals. With such a configuration, the first O-ring 74 is not degraded by the medicinal solution and the like used in the cleaning processing, the disinfecting processing, and the sterilizing processing, etc., and is capable of surely maintaining the sealability to the expected temperature changes in the cleaning processing, the disinfecting processing, and the sterilizing processing, etc. Therefore, it is possible to surely prevent moisture and the like from intruding into the optical connector plug 36 during the cleaning processing, the disinfecting processing, the sterilizing processing and the like.

The second O-ring 75, which seals the part of the optical connector plug 36 on the proximal end side with respect to the glass member 72, is made of the ethylene propylene rubber having the glass transition point (glass transition point of −60° C.) lower than that of the butyl rubber. With such a configuration, the second O-ring 75 is capable of surely maintaining the sealability even in the case where the temperature at the time of the air transportation or the like decreases to a temperature equal to or lower than the glass transition point of the first O-ring 74 and the sealing performance of the first O-ring 74 degrades. Therefore, even under a low temperature environment such as air transportation, it is possible to surely prevent the intrusion of moisture and the like into the optical connector plug 36.

In addition, the first O-ring 74 and the second O-ring 75 are compressed between the inward flange 71 and the cap member 73 until the O-rings are flattened by approximately 30% to 40% relative to their natural state. Therefore, the first O-ring 74 and the second O-ring 75 can be surely brought into close contact with the glass member 72 and the sleeve 65, to thereby ensure the sufficient sealability.

In addition, the adhesive 72a is applied between the sleeve 65 and the glass member 72, to thereby enable the sealability between the sleeve 65 and the glass member 72 to be improved. In this case, the first O-ring 74, which is highly resistant to the degradation due to the chemicals, is provided on the distal end side with respect to the glass member 72 (between the glass member 72 and the cap member 73), to thereby be capable of surely prevent the degradation of the adhesive 72a due to the medicinal solution.

In addition, the inside of the sleeve 65 is filled with the inert gas 76 such as argon or nitrogen, and the inert gas 76 accounts for 80% or more of the volume of the gaseous body in the sleeve 65, to thereby surely suppress the occurrence of the moisture condensation in the optical connector plug 36 even in the case where the rapid temperature changes occur.

Figure 7:
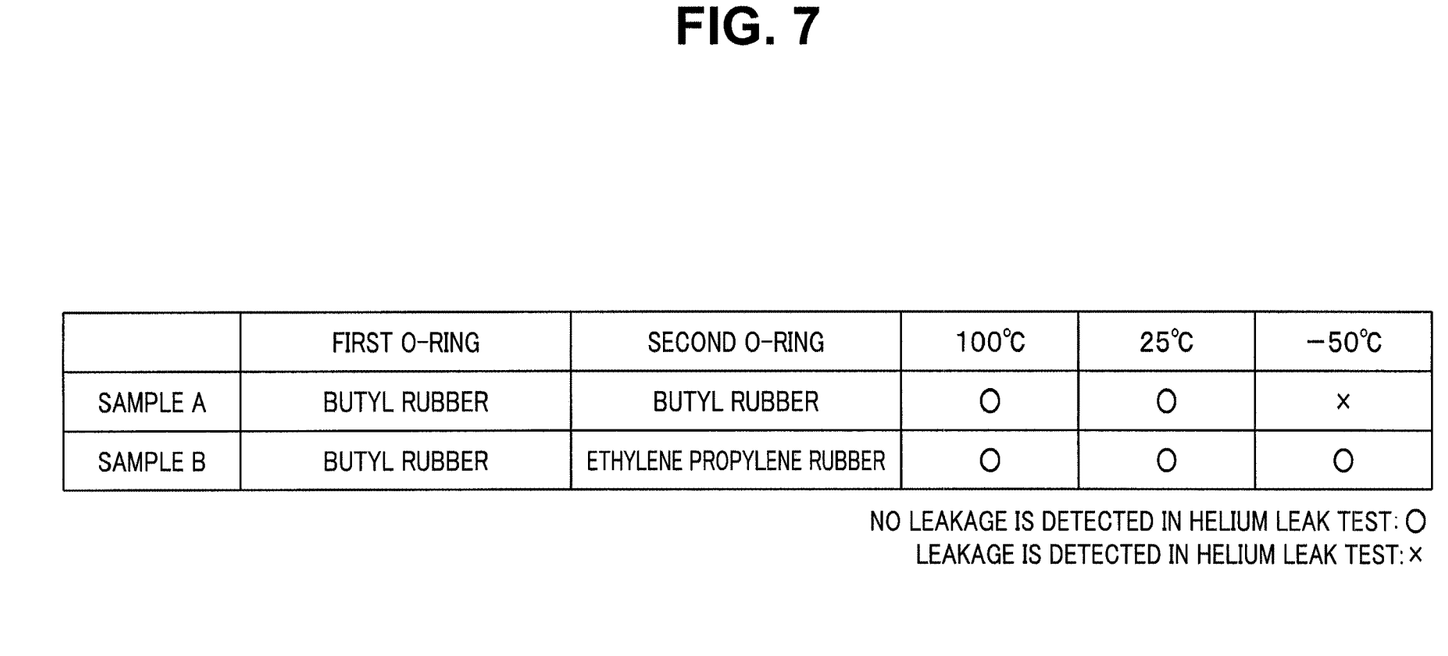
FIG. 7 is a chart showing reliability results in a heat shock test and a high-temperature and high-humidity test.
Figure 8:
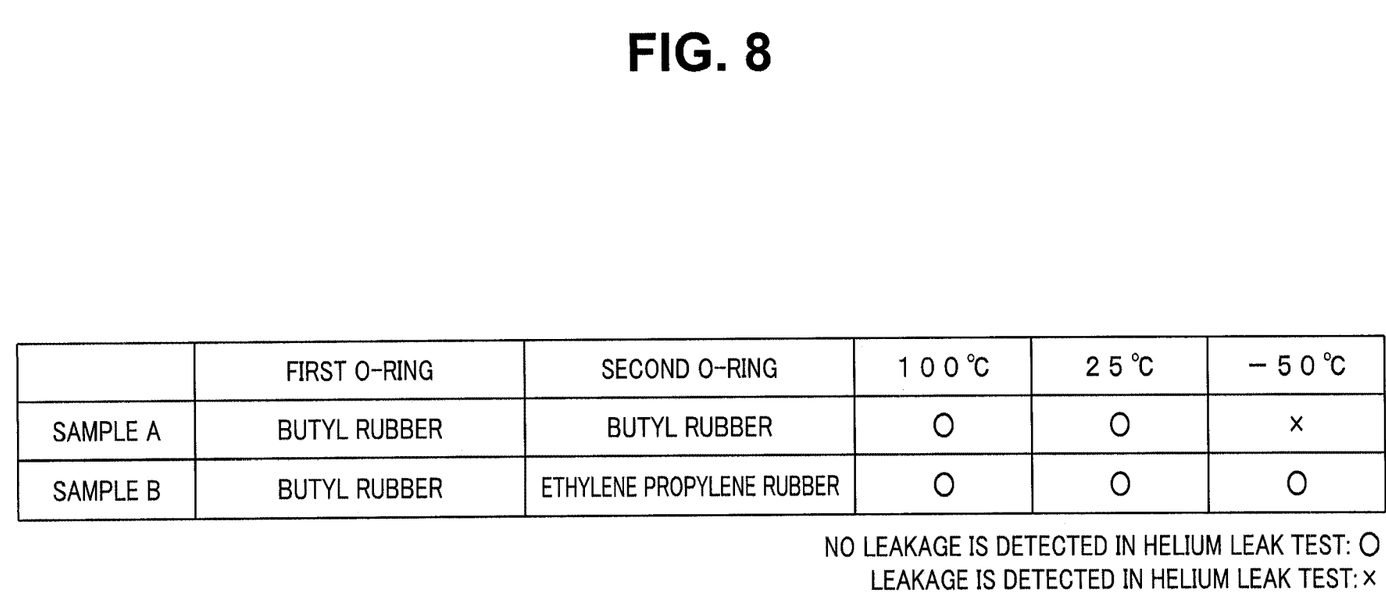
FIG. 8 is a chart showing a reliability result in a sterilization test.
Figure 9:
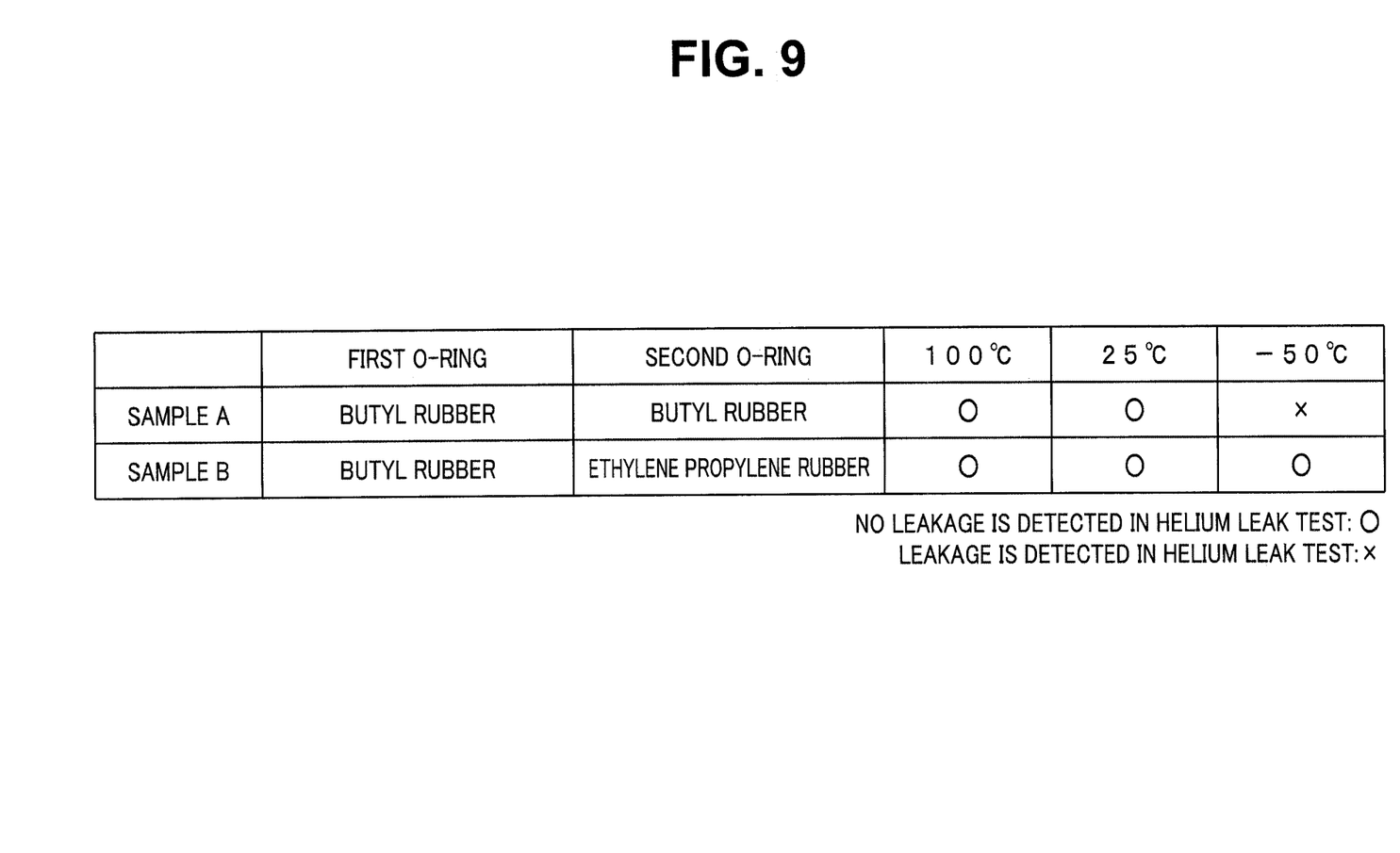
FIG. 9 is a chart showing a reliability result in a washer disinfector test.

Here, results of various kinds of leak tests for the optical connector plug 36 according to the present embodiment are shown in FIGS. 7 to 9.

In each of the drawings, a sample A shows an optical connector plug as a comparative example in which both the first and second O-rings 74 and 75 are made of the butyl rubber. On the other hand, a sample B shows the optical connector plug 36 according to the present embodiment in which the first O-ring 74 is made of the butyl rubber and the second O-ring 75 is made of the ethylene propylene rubber. Note that, the test described here is a helium leak test. As one example, the test is performed using a vacuum method in which a helium gas is supplied to the outside of the optical connector plug 36, instead of the argon gas, and passage of the helium gas is detected by evacuating the inside of the optical connector plug of each of the sample A and the sample B.

The result of the leak test shown in FIG. 7 is an evaluation result of a leak reliability test after performing a heat shock test (40 to 80 cycles) and a high-temperature and high-humidity test (600 to 800 hours) alternately on the optical connector plug of each of the sample A and the sample B.

In the heat shock test, one cycle is defined as a duration in which each of the samples is left under a temperature (80° C., for example) higher than a room temperature for a predetermined time period (for several tens of minutes, for example, 30 minutes), and after that, each of the samples is left under an environment below the freezing point (−40° C., for example) for a predetermined time period (for several tens of minutes, for example, 30 minutes). In addition, in the high-temperature and high-humidity test, each of the samples is left under an environment at a temperature higher than the room temperature and at a predetermined relative humidity close to 100% (ambient temperature is 60° C. and humidity is 90%, for example).

After the completion of all the heat shock tests and the high-temperature and high-humidity tests, the leak test has been performed under the three kinds of temperature environments (100° C., 25° C., and −50° C.).

As shown in FIG. 7, it can be confirmed that a leakage was detected in the sample A at −50° C., on the other hand, no leakage was detected in the sample B at any of the temperatures.

The result of the leak test shown in FIG. 8 is an evaluation result of a leak reliability test after performing hydrogen peroxide low temperature plasma sterilization tests (100 to 300 cases) on the optical connector plug of each of the sample A and the sample B. In the sterilization test, one cycle is defined as sterilization in the advanced cycle using STERRAD® (registered trademark) NX sterilization apparatus (whether or not to include ALL Clear Technology) made by ASP (Advanced Sterilization Products), for example.

After the completion of all the sterilization tests, the leak test has been performed under the three kinds of temperature environments (100° C., 25° C., and −50° C.).

As shown in FIG. 8, it can be confirmed that a leakage was detected in the sample A at −50° C., on the other hand, no leakage was detected in the sample B at any of the temperatures.

The result of the leak test shown in FIG. 9 is an evaluation result of a reliability test after performing washer disinfector tests (100 to 300 cases) on the optical connector plug of each of the sample A and the sample B. The cleaning solution is Sekumatic-FR (made of Henkel-Ecolab) mainly composed of phosphate and strong alkali (pH14), for example. After the completion of all the washer disinfector tests (100 to 300 cases), the leak test has been performed under the three kinds of temperature environments (100° C., 25° C., and −50° C.).

As shown in FIG. 9, it can be confirmed that a leakage was detected in the sample A at −50° C., on the other hand, no leakage was detected in the sample B at any of the temperatures.

As is clear from the results of these tests, the optical connector plug 36 of the present embodiment is capable of maintaining the sealability between the glass member 72 and the sleeve 65 while preventing occurrence of a leakage in all the expected temperature ranges even if the optical connector plug 36 is used repeatedly.

Note that the present invention is not limited to the above-described embodiment, but various modifications and changes are possible, and such modifications and changes are also within the technical range of the present invention. In the above-described embodiment, for example, the optical connector plug 36 has a function of transmitting (emitting) the optical signal such as the image signal and the like to the processor 3. However, the present invention is not limited to the optical connector plug having such a function. For example, the optical connector plug 36 may have a function of receiving (allow the incident of) the optical signal such as the control signal from the processor 3. Alternatively, the optical connector plug 36 may have functions of transmitting and receiving (emitting and allowing the incidence of) the optical signal to and from the processor 3.

What is claimed is:

1. An endoscope optical connector comprising:
    a cylindrical member configured to house an end portion of an optical transmission member inside the cylindrical member;
    a positioning member provided on an inner circumference of the cylindrical member;
    a light-passing member arranged inside the cylindrical member so as to face an end surface of the optical transmission member;
    a fixing member attached to the cylindrical member, and configured to fix the light-passing member between the fixing member and the positioning member;
    a first elastic sealing member interposed between the fixing member and the light-passing member;
    a second elastic sealing member interposed between the light-passing member and the positioning member, the second elastic sealing member having a glass transition point lower than a glass transition point of the first elastic sealing member; and
    gas filling the inside of the cylindrical member.

2. The endoscope optical connector according to claim 1, wherein
    the first elastic sealing member has a heat resistance limit temperature of 150° C., the glass transition point of −50° C., and a higher resistance to degradation due to chemicals than the second elastic sealing member, and
    the second elastic sealing member has the glass transition point of −60° C.

3. The endoscope optical connector according to claim 2, wherein the first elastic sealing member includes a butyl rubber, and the second elastic sealing member includes an ethylene propylene rubber.

4. The endoscope optical connector according to claim 1, wherein the fixing member compresses the first elastic sealing member and the second elastic sealing member between the fixing member and the positioning member until the first elastic sealing member and the second elastic sealing member are flattened by 30% to 40% relative to natural states of the first elastic sealing member and the second elastic sealing member.

5. The endoscope optical connector according to claim 1, wherein an adhesive is applied between the cylindrical member and the light-passing member.

6. The endoscope optical connector according to claim 1, wherein the optical transmission member transmits an optical signal.

7. The endoscope optical connector according to claim 1, wherein the gas filling the inside of the cylindrical member is an inert gas.

8. The endoscope optical connector according to claim 7, wherein the inert gas accounts for 80% or more of a volume of a gaseous body in the cylindrical member.

9. An endoscope comprising an optical connector as an endoscope connector,
    the optical connector comprising:
        a cylindrical member configured to house an end portion of an optical transmission member inside the cylindrical member;
        a positioning member provided on an inner circumference of the cylindrical member;
        a light-passing member arranged inside the cylindrical member so as to face an end surface of the optical transmission member;
        a fixing member attached to the cylindrical member, and configured to fix the light-passing member between the fixing member and the positioning member;
        a first elastic sealing member interposed between the fixing member and the light-passing member;
        a second elastic sealing member interposed between the light-passing member and the positioning member, the second elastic sealing member having a glass transition point lower than a glass transition point of the first elastic sealing member; and
        gas filling the inside of the cylindrical member.

10. An endoscope optical connector comprising:
    a cylindrical member configured to house an end portion of an optical transmission member inside the cylindrical member;
    a positioning member provided on an inner circumference of the cylindrical member;
    a light-passing member arranged inside the cylindrical member so as to face an end surface of the optical transmission member;
    a fixing member attached to the cylindrical member, and configured to fix the light-passing member between the fixing member and the positioning member;
    a first elastic sealing member interposed between the fixing member and the light-passing member;
    a second elastic sealing member interposed between the light-passing member and the positioning member; and
    gas filling the inside of the cylindrical member, wherein
    the first elastic sealing member has a higher resistance to degradation due to chemicals than the second elastic sealing member, and
    the second elastic sealing member ensures a higher sealability between the cylindrical member and the light-passing member under an environment of a temperature of −50° C. than the first elastic sealing member.

* * * * *